US00PP10470P

United States Patent [19]

van Andel

[11] Patent Number: Plant 10,470

[45] Date of Patent: Jun. 30, 1998

[54] FREESIA PLANT VARIETY NAMED 'VARABLUE'

[75] Inventor: Jacob van Andel, Aalsmeer, Netherlands

[73] Assignee: Van Staaveren B.V., Aalsmeer, Netherlands

[21] Appl. No.: 814,542

[22] Filed: Mar. 10, 1997

[51] Int. Cl.[6] ..... A01H 5/00

[52] U.S. Cl. ..... Plt./83

[58] Field of Search ..... Plt./83

[56] References Cited

U.S. PATENT DOCUMENTS

P.P. 32 1/1932 Dalrymple ..... Plt./83
P.P. 98 6/1934 Morgan ..... Plt./83

*Primary Examiner*—James R. Feyrer
*Assistant Examiner*—Kent L. Bell
*Attorney, Agent, or Firm*—Christie, Parker & Hale,LLP

[57] ABSTRACT

A new plant variety of freesia with early flowering response suitable for growing as a cut flower.

1 Drawing Sheet

BACKGROUND OF THE INVENTION

This invention relates to a new and distinct variety of Freesia which originated by crossing two unpatented, unnamed varieties of this creation at the Van Staaveren Nursery in Aalsmeer, the Netherlands. The female parent is identified as 3208-AT-1 and the male parent is identified as 841-J.

SUMMARY OF THE INVENTION

Among the features which distinguish the new variety from other presently available and known commercial cultivars are attractive flowers and early flowering response after planting which distinguishes the new variety to be suitable as a cut flower variety. Asexual reproduction of the new variety by corms and cormlets in Aalsmeer, The Netherlands has established that the distinctive characteristics are transmitted through succeeding generations. The varietal denomination of the new variety is 'Varablue'.

FLOWERING TIME

Under conditions of growing plants under glass in The Netherlands, Freesia plant varieties typically flower in about 22 to 23 weeks for plants planted in October; about 21 to 22 weeks for plants planted in December/January; and about 20 to 30 weeks for plants planted in June/July (flowering depends on soil temperature after about 20 to 30 weeks). In contrast to the above, the flowering time after planting in October for 'Varablue' is about 18 weeks, about 16 weeks and about 16 weeks for October planting, January planting and June planting, respectively, under glass in Aalsmeer, The Netherlands.

BRIEF DESCRIPTION OF ILLUSTRATION

The accompanying photograph illustrates the new variety and shows the flowering thereof from bud to full bloom depicted in color as nearly correct as it is possible to make in a color illustration of this character. Throughout this description, color values are based upon The Colour Chart of The Royal Horticultural Society of London, England, except where common terms of color definition are employed.

DESCRIPTION OF THE NEW VARIETY

The following description is of Pot Freesia Plants of the new cultivar grown under glass in Aalsmeer, Netherlands, during the month of November. Phenotyphic expression may vary with environment, cultural and clematic conditions, as well as differences and conditions in light, soil, and temperature.

Plant

A. *Form.*—Upright.

B. *Growth.*—Height attained: Up to about 100 cm. Branching: No.

C. *Flower stem.*—1. Length: Up to about 100 cm. long. 2. Color: Near 143A.

D. *Foliage.*—1. Quantity: Relatively small. 2. Size: Length — ±about 100 cm. Width — ±about 1.5 cm. 3. Shape of leaf: Oblongate. 4. Texture: Smooth (top side and underside). 5. Color: Near 143A (top side and underside). 6. Veination: yes, normal. 7. Stem color: Near 143A. 8. Corms: Color: Brown with brown scales. Size: Varying.

*The bud stage.*—A. Bud form: Long ovate. B. Bud size: About 15 mm×55 mm. C. Opening rate: Medium. D. Color: 1. When petals first divide: Near 92B. 2. When petals begin to unfurl: Near 92B. 3. When flowers open (inner petals): Top — near 92B. Bottom — near 155D with some blue stripes near 92B. (outer petals): Top — near 92B. Bottom — near 155D with some blue stripes near 92B. 4. Calyx: Shape — tubular. Size — small.

The flower stage:

A *Inflorescence.*—1. Blooming habit: Intermittent. 2. Approximate number of flowers: 8 to 9. 3. Form: Cup. 4. Type: Raceme. 5. Diameter: About 55 mm×70 mm.

B. *Response* (*time from pinch*).—Early. 1. Type: Single. 2. Form: Intermittent. 3. Borne: Raceme. 4. Size: About 55 mm×70 mm. 5. Shape: Cup. 6. Color tonality from a distance: Blue. 7. Lasting quality (days) on plant: Long, over 14 days.

B *Flower color.*—1. Flower coloration: Violet-Blue. 2. Inner petals: Top near 92B — botton near 155D 3. Outer petals: Top near 92B — bottom near 155D. 4. Point of petal attachment: Near 13A. 5. Discoloration as bloom ages: Slight discoloration (lighter blue). 6. Petals: Number of petals: 6. Arrangement: Tubular. Texture: Soft. Shape: Broad elliptic. 7. Color: Near 92B (top and underside).

C. *Persistence.*—18 days on the plant, 8 days after cutting.

D. *Fragrance.*—None.

Reproductive organs:

A. *Stamens, filaments and anthers.*—1 Stamens: Triple forked, violet. 2. Anthers: 3 singles. Color — violet top, white bottom, yellow. 3. Filaments: base. Violet. 4. Pollen: White to yellow.

B. *Pistils.*—1 Styles: 3. 2. Stigmas: 1.

C. *Character of ovaries.*—Cylindrical.

D. *Calyx shape.*—Shape: Funnel. Size: About 8–12 mm.

I claim:

1. A new and distinct variety of freesia plant substantially as described and illustrated herein.

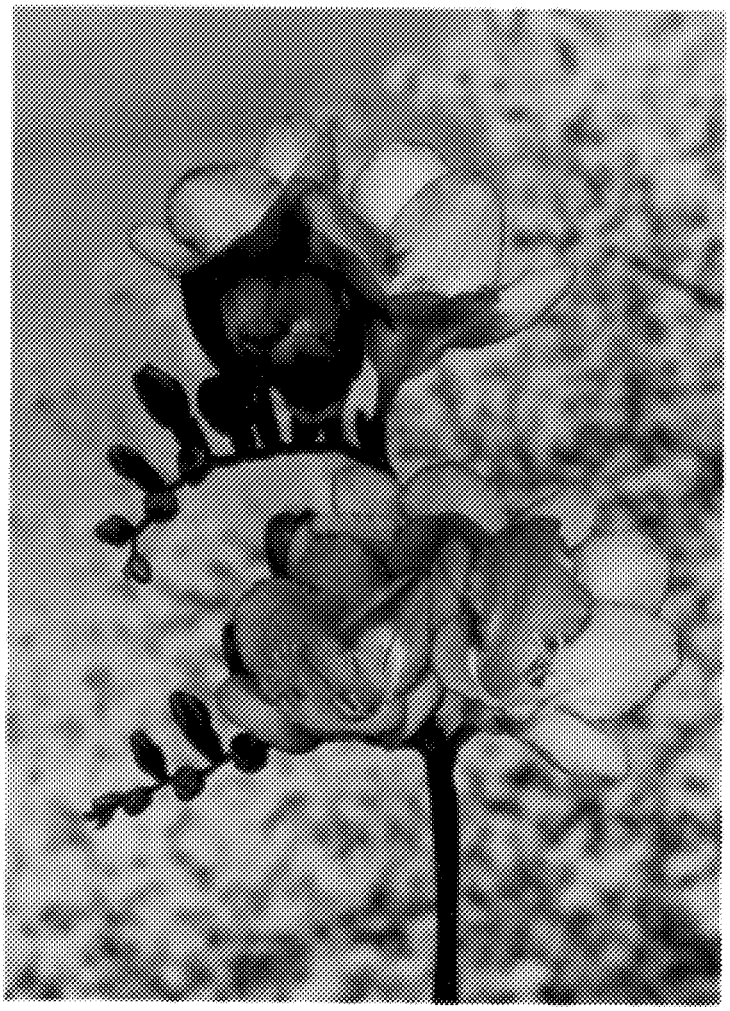

* * * * *